United States Patent [19]

Cohen et al.

[11] 4,256,385

[45] Mar. 17, 1981

[54] CORNEA-EXAMINING INSTRUMENT

[75] Inventors: Samuel W. Cohen; Settimio Infantino, both of Brooklyn, N.Y.

[73] Assignee: Velotron Machine Corp., Brooklyn, N.Y.

[21] Appl. No.: 14,080

[22] Filed: Feb. 22, 1979

[51] Int. Cl.³ .............................................. A61B 3/10
[52] U.S. Cl. ........................................ 351/13; 351/16
[58] Field of Search .......................... 351/6, 13, 16, 12

[56] References Cited

U.S. PATENT DOCUMENTS

| | | | |
|---|---|---|---|
| 3,542,458 | 11/1970 | Volk | 351/13 |
| 3,861,789 | 1/1975 | Heine | 351/12 |
| 4,046,463 | 9/1977 | La Russa | 351/13 |

OTHER PUBLICATIONS

Keeler, Keelers Klein Keratoscope, Joun. of American Optom. Assoc., 5/77.

Primary Examiner—John K. Corbin
Assistant Examiner—Rodney B. Bovernick
Attorney, Agent, or Firm—Bertram Frank

[57] ABSTRACT

A cornea-examining instrument includes a plate-shaped examining element of a transparent material, which has at least one light-reflective formation on one end face thereof. The examining element has a bore which extends generally parallel to said one face. A light source, particularly a penlight, has a mounting portion which is accommodated in the bore and through which a beam of light is emitted into the transparent examining element to illuminate the formation so that light reflected therefrom forms an image of the formation on the cornea being examined when a main axis of the examining element intersects the cornea, the shape of the image being indicative of the shape of the cornea. The formation can consist of a continuous groove or a plurality of spaced depressions. When a plurality of the formations is provided, they may be shaped as parallel straight lines symmetrically arranged with respect to the main axis, or as concentric rings. In the latter event, the depressions are preferably radially aligned with one another as between the formations so that the axes of corneal asphericity can be determined. The periphery of the examining element may be provided with an inwardly facing light-reflective layer to reflect light rays back into the examining element, and a bore centered on said main axis provided for examining the cornea therethrough. A magnifying lens may be pivotally mounted on the examining element adjacent the end face carrying the formation.

19 Claims, 8 Drawing Figures

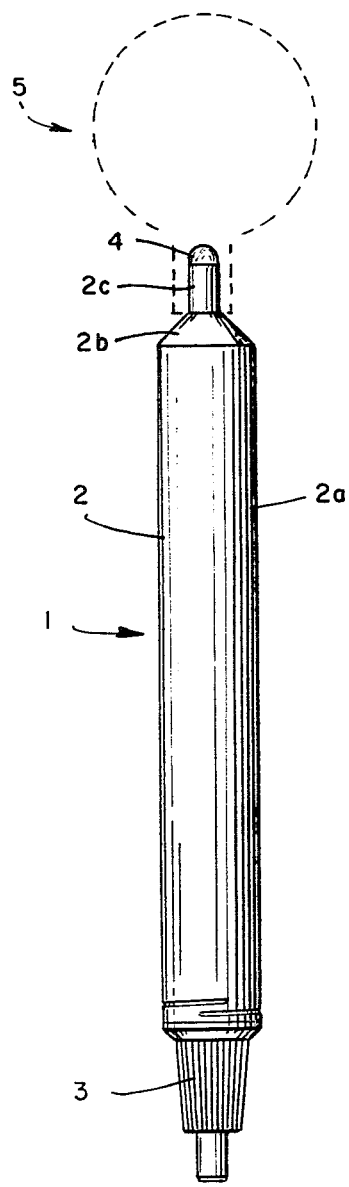
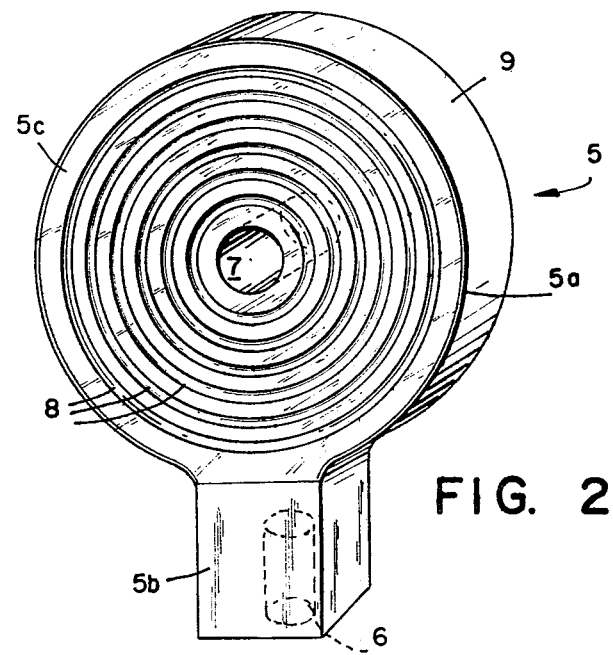
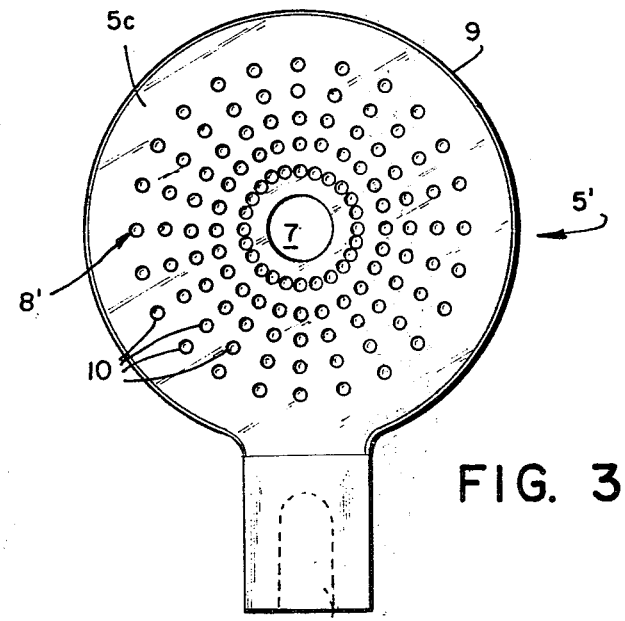
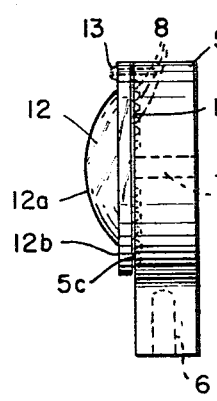

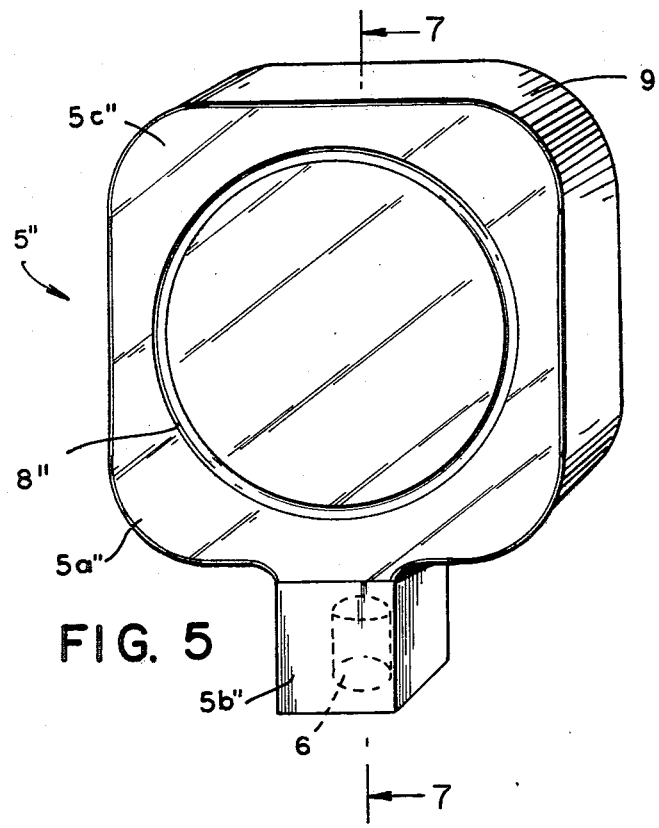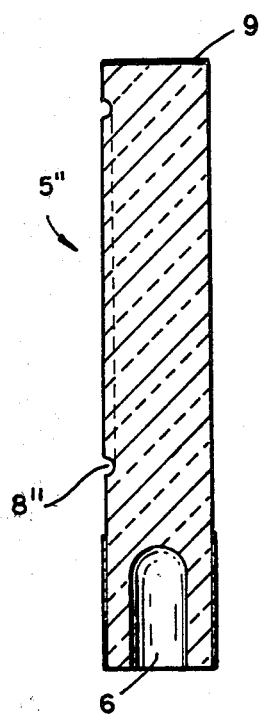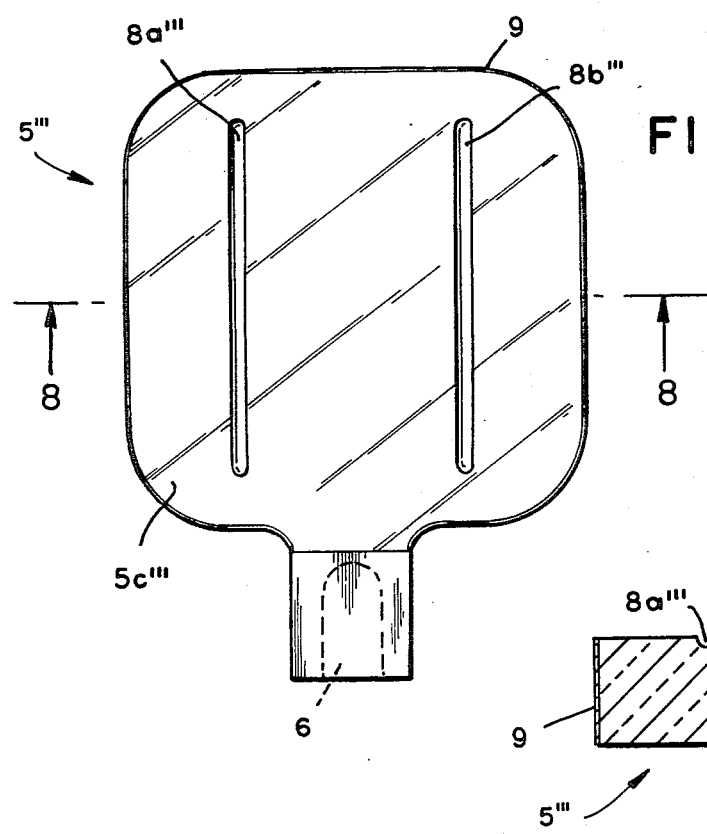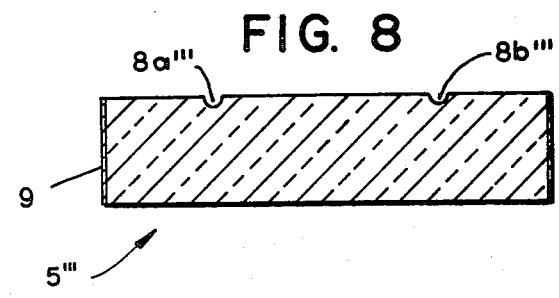

CORNEA-EXAMINING INSTRUMENT

BACKGROUND OF THE INVENTION

The present invention relates to an eye-examining instrument in general, and more particularly to an instrument by means of which the shape of the cornea of the eye can be determined.

In many instances, it is necessary to determine the corneal radius of an eye, usually in more than one plane. One of these instances, possibly the most important one but not the only one, is encountered in the making or fitting of hard or soft contact lenses where the concave surface of the respective contact lens will have to conform, to the largest feasible extent, to the shape of the outer surface of the cornea to obtain a good fit which will not only reduce if not eliminate any discomfort perceived by the wearer of the contact lens, but will also minimize the possibility that air inclusions or bubbles could be trapped between the external surface of the cornea and the concave surface of the contact lens.

The need for making this determination and taking the appropriate measurements has been recognized a long time ago and various instruments have been proposed for accomplishing this purpose. So, for instance, the U.S. Pat. No. 3,797,921, issued on Mar. 19, 1974, discloses a photographing apparatus for determining corneal radius. This apparatus has substantial dimensions so that it has to be stationarily mounted on a support in an examination room. This apparatus has a generally tubular casing which, at its end facing the patient, carries a part-spherical focusing screen having a plurality of transparent circles thereon. Light from a source located within the casing passes through the transparent circles onto the cornea being examined to form a plurality of ring-shaped images on the cornea. These images are then photographed by a camera located at the end of the casing which is remote from the focusing screen, through a tubular element passing through the center of the focusing screen. Besides being bulky and hence usable only in the examination room setting, this apparatus is also disadvantageous in that the light from the light source is unevenly distributed between the individual transparent circles as well as within each circle, which renders a proper evaluation of the photograph of the cornea and the images of the circles formed thereon difficult. Also, in the event that the cornea is aspherical, that is, when it has different radii of curvature in different planes including and intersecting the axis of the apparatus and the coincident axis of the cornea, it is very difficult to establish the degree and orientation of the asphericity, especially when the variations in the radius of curvature are quite small.

This latter problem is avoided, at least to a certain degree, in the apparatus disclosed in the U.S. Pat. No. 4,046,463, granted on Sept. 6, 1977, wherein a plurality of lamps is provided at the end of the apparatus which faces the patient, the lamps being uniformly distributed on a circle centered on the axis of the apparatus. Thus, an individual image of each of the lamps is formed on the cornea of the eye being examined and the radii of curvature of the cornea in various planes can be determined by measuring the distance between the images which are located diametrically opposite in the respective plane. Here again, the apparatus is very bulky and thus suitable for use only in the environment of an examination room. Furthermore, the rather intense light emitted by the lamps inconveniences the person being examined and may even cause some involuntary eyelid movements which then would interfere with the proper movements. In addition thereto, the provision of the lights on just a single circle does not permit a thorough examination of the cornea and all its possible peculiarities.

SUMMARY OF THE INVENTION

Accordingly, it is a general object of the present invention to avoid the disadvantages of the prior art.

More particularly, it is an object of the present invention to provide a cornea-examining instrument which is not possessed of the disadvantages of the prior-art devices of this type.

Still another object of the present invention is to develop a cornea-examining instrument which is simple in construction, has small dimensions and hence is portable, and is easy to use, giving accurate indications nevertheless.

A further object of the present invention is to so construct the instrument as to be usable outside, as well as inside, an examination room.

A concomitant object of the present invention is to devise an instrument of the above type which is very lightweight and compact and hence readily portable from one location to another.

In pursuance of these objects and others which will become apparent hereafter, one feature of the present invention resides in a pocket-type instrument for determining the shape of a cornea of an eye which, briefly stated, comprises an examining element of a transparent material having at least one light-reflective formation thereon centered on an axis; and a portable source of light so positioned relative to the examining element that a light beam emitted thereby is directed transversely of the axis to illuminate the formation and to be reflected thereby onto the cornea being examined when the above-mentioned axis intersects the same, forming an image of the formation on the cornea, the shape of such an image being indicative of the shape of the cornea. The formation may have an annular configuration, or may include two separate straight-lined parallel sections.

One of the main advantages of the above-discussed construction of the instrument is that it can be carried by the ophthalmologist, optometrist, or any other person licensed to examine the cornea, to any location, even to the bedside of a bed-ridden patient. Another advantage is that only reflected light is directed against the eye of the patient so that the examination does not cause the patient to feel any discomfort. Still, the intensity of the image of the formation is sufficient for the examining person to be able to make an accurate determination of the shape of the cornea being examined.

Advantageously, the examining element is substantially plate-shaped and has two axial end surfaces, and the formation is situated at one of the end surfaces. Then, it is especially advantageous when the formation includes at least one depression extending from the one end surface into the examining element. The plate-shaped configuration eliminates the possibility of undesired distortions and has the advantages which will become apparent as the description proceeds. The provision of the formation as a depression is advantageous not only from the manufacturing standpoint, but also because the surfaces which bound the depression constitute obstructions in the path of light emanating from the light source so that they can themselves reflect the light impinging upon the same, particularly if these surfaces have a matte finish. However, the light-reflective action of the depression may be made even more pronounced when a layer of light-reflective, especially light-scattering, paint is provided in the depression.

The depression can be configurated as a continuous circular groove centered on the aforementioned axis. It is further advantageous when the examining element is provided with at least one additional continuous circular groove centered on said axis and radially spaced from the above-mentioned groove. When these expedients are resorted to, the images formed on the cornea will be continuously annular, either circular in the event that the cornea does not have any astigmatism, or deviating from the circular shape in the event that the cornea is aspherical. The extent of such a deviation will then be indicative of the extent and orientation of the asphericity. However, an even more accurate determination of the sphericity can be made when each of the formations, according to the further aspect of the present invention, includes a plurality of the above-mentioned depressions which are circumferentially spaced from one another, and when associated ones of the spaced depressions of all of the formations are aligned with one another radially of the axis. When the individual depressions are provided in the above-mentioned manner, it is then possible to accurately determine the axes of asphericity of the cornea being examined.

According to an additional facet of the present invention, the examining element has a periphery which extends parallel to the aforementioned axis. The periphery may either be substantially cylindrical and centered on the above-mentioned axis, or polyhedral. Then, an inwardly facing light-reflective layer is provided on the periphery for reflecting light rays reaching the periphery back into the examining element. In this manner, the light rays which would otherwise escape from the examining element are reflected back into the same to illuminate the annular formations.

In a currently preferred embodiment of the present invention, the examining element has an extension which projects substantially radially from the periphery of the examining element and which has a radial bore therein. The light source has a mounting portion which is coaxial with the beam of light emitted thereby and which is removably accommodated in the bore when assembled with the examining element. Thus, in the assembled condition, the source of light will emit light rays into the transparent element and the light source, which is suitably constructed as a penlight, can be utilized as a handle for holding the assembly during the examination. On the other hand, the removable accommodation of the mounting portion in the bore renders it possible to disassemble the two components from one another for separate transportation, which further improves on the portability of the instrument, or for ready interchange of the above-discussed examining elements with one another or with other attachments. Also, when no examining element is mounted on the mounting portion, the light source can be used in the manner of a standard ophthalmic penlight, for instance, for examining the retina of the eye or for similar purposes.

It is further advantageous when the extension of the examining element, which has an internal surface bounding the bore and an external surface spacedly surrounding the internal surface, is provided with an inwardly facing light-reflecting layer on one of the surfaces. When this expedient is used, light rays, which would otherwise escape from the examining element through the external surface of the extension, are reflected back and thus directed into the disc-shaped portion of the examining element.

A further feature of the present invention resides in the provision of the examining element with a substantially plate-shaped portion which has the above-mentioned formations, and a lens portion which is coaxially juxtaposed with at least a region of the plate-shaped portion for examination. In this manner, the examiner obtains a magnification of the cornea and of the images of the formations formed thereon, thus improving the accuracy of the determination of the corneal radius or radii. In this context, it is particularly advantageous when, in accordance with the invention, the portions of the examining element are discrete members which are displaceably mounted on one another. Herein, it is especially appropriate, both for manufacturing and use considerations, when the lens member is mounted at the periphery of the plate-shaped member by a pivot. In this manner, the lens member can be pivoted into a coaxial position for magnification, or can be pivoted away for examination without magnification.

It is possible and advantageous to so construct the examining element that the cornea can be observed through an unobstructed central region of the examining element. However, it has been found to be advantageous, for some applications, to provide the examining element with a hole which surrounds the axis. A twofold advantage is obtained from this construction. On the one hand, the provision of the hole permits the direct observation of the cornea therethrough without any distortion, no matter how minute, which occurs when the same space is occupied by the transparent material constituting the remainder of the examining element. On the other hand, the internal surface bounding the hole serves as a guidance to the eye-examining doctor for bringing the axis of the examining element in conformity with the axis of the cornea being examined.

It may be seen from the above explanation that the present invention provides a cornea-examining instrument which satisfies the above-enumerated objects and which particularly is very versatile, renders possible a quick and accurate determination of the shape of the cornea being examined, and can be easily transported or carried from one location to another.

Other aspects and advantages of the invention will become more apparent by reference to the following detailed description when considered in connection with the accompanying drawings in which the same or similar reference numerals designate like or corresponding parts throughout the various views.

BRIEF DESCRIPTION OF THE DRAWINGS

FIG. 1 is a side elevational view of a penlight constituting one component of the instrument of the present invention;

FIG. 2 is a perspective view of an examining element constituting another component of the instrument;

FIG. 3 is a front elevational view of a modified examining element;

FIG. 4 is a side elevational view of the examining element of FIG. 2 or 3 equipped with a lens portion.

FIG. 5 is a perspective view of another modified examining element;

FIG. 6 is a front elevational view of a still other modified examining element;

FIG. 7 is a sectional view taken on line 7—7 of FIG. 5; and

FIG. 8 is a sectional view taken on line 8—8 of FIG. 6.

DETAILED DESCRIPTION OF THE PREFERRED EMBODIMENTS

Referring now to the drawings in detail, and first to FIG. 1 thereof, it may be seen that the reference numeral 1 designates a portable light source, particularly a penlight, in toto. The light source 1 has a housing 2 which, in a conventional manner, accommodates a battery or several batteries. The housing 2 has a substantially cylindrical portion 2a which accommodates the battery or batteries, a substantially cylindrical mounting portion 2c at one end of the cylindrical portion 2a, and a substantially conical intermediate portion 2b which forms a transition between the portions 2a and 2c. A light bulb 4 is rigidly mounted in the mounting portion 2c, and a switch 3 is mounted at the opposite end of the cylindrical portion 2a. At least the cylindrical portion 2a is made of an electrically conductive material and is connected to one contact of the light bulb 4, while one terminal of the battery or batteries is connected to the other contact of the light bulb 4. The switch 3 is in electrical contact with another terminal of the battery or batteries and is also electrically connected to the cylindrical portion 2a and thus interposed in an electrical circuit including the battery or batteries and the light bulb. Thus, when the switch 3 is activated, that is, when it closes the circuit, the light bulb 4 will generate light. On the other hand, the deactivation of the switch 3 will interrupt the electric circuit and, consequently, no light will be emitted by the light bulb 4.

FIG. 2 illustrates an examining element 5 which, as may be seen, includes a generally disc-shaped portion 5a, and a radial extension 5b integral with the disc portion 5a. The examining element 5 is made of a transparent material, especially of a polymer of an acrylic acid or an ester thereof, such as polymeric methacrylate which is currently commercially available under the trademark Lucite. This material possesses good optical properties and, more particularly, it exhibits a very low amount of optical distortion. On the other hand, this material can be very easily shaped by molding, material-removing techniques, and the like.

The disc-shaped portion 5a has an end face 5c which has a plurality of light-reflective annular formations 8 thereon. The formations 8 are centered on an axis of the disc-shaped portion 5a, and a through hole 7 is provided in the portion 5a and is also centered on the same axis.

A layer 9 of an inwardly facing light reflective material may be provided at least on the periphery of the disc-shaped portion 5a. However, the layer 9 may also extend onto the external surface of the extension 5b.

A bore 6 extending radially of the axis of the disc-shaped portion 5a is provided in the extension 5b. The dimensions of the bore 6 are such that the mounting portion 2c of the light source 1 illustrated in FIG. 1 can be fittingly but removably accommodated therein. The surface bounding the bore 6 may be provided with a layer of light-reflective material, either in addition to, or instead of, the layer 9 provided on the external surface of the extension 5b.

In operation, the light source 1 and the examining element 5 may be transported in a disassembled condition to the location of intended use. Thereat, the light source 1 may either be used alone in the same manner as conventional eye-examining penlights, or it can be assembled with the examining element 5 by introducing the mounting portion 2c with the light bulb 4 of the light source 1 into the bore 6 of the examining element 5. Once this is done, the cylindrical portion 2a of the light source 1 can be used as a handle for the examining element 5.

Then, the assembled instrument is so held between the eye of the examining physician and that of the person being examined that the physician can see the cornea of the patient's eye through the hole 7 and conform the axis of the hole 7 and thus of the entire disc-shaped portion 5a with that of the cornea to be examined. The switch 3 is activated either prior to or subsequently to the alignment so that the light bulb 4 will emit light rays which will propagate from the extension 5b into the disc-shaped portion 5a of the examining element 5. These light rays will impinge upon the formations 8, and will be reflected thereby toward the cornea being examined so that images of these formations will be formed on the cornea. The shape of these images will be observed through the hole 7 by the examining physician or optometrist. The shape and spacing of these images will then enable the examiner to determine the curvature of the cornea being examined.

So long as the cornea is spherical, the images of the formations 8 will appear at regular intervals. Should the cornea be aspherical but still axially symmetrical, the intervals between the images of the formations 8 on the cornea will vary, but the images will remain circular. It is only when the cornea is astigmatic, that is, when it has different radii of curvature in various radial planes that the shape of the images will change from circular to elliptical or the like. When this happens, the ophthalmologist conducting the examination will be able to estimate the degree and orientation of the astigmatism.

A more accurate determination of the extent and orientation of the astigmatism is obtained when an examining element 5' illustrated in FIG. 3 is used. This examining element 5' is in many respects identical to that of FIG. 2, except that each of the annular formations, here designated as 8', includes a plurality of dot-like elements 10 which are regularly distributed over the circumference of the respective formation 8'. The associated elements 10 of the respective formations 8' are aligned with one another in the radial direction in respective radial rows. Advantageously, there are 24 of such rows each extending radially outwardly from the axis of the hole 7, so that the neighboring rows of the element 10 are angularly spaced from one another by 15°.

The operation of this examining element 5' is the same as that discussed above in connection with the examining element 5 except that the arrangement of the individual elements 10 of the formations 8' in the radial rows renders it possible to accurately determine, within the range of accuracy afforded by the angular spacing of the rows, the location of the major and minor axes of the corneal astigmatism. It will be appreciated that those elements 10 which are located close to the major axis of the corneal astigmatism will be spaced the farthest apart, while those located at the minor axis will be closest to one another. Hence, a much more accurate determination of the corneal astigmatism may be obtained by using the examining element 5' than when the examining element 5 is being used.

In both instances, the reflective layer 9, if such is provided, will reflect those light rays which reach the periphery or external surface of the respective examining element, and which would otherwise escape out of the examining element 5 or 5', back into the same, thus providing further illumination for the formations 8 or 8', intensifying the images thereof on the cornea.

As may be seen in FIG. 4, the formations 8 and, similarly, the elements 10 of the formations 8', are advantageously formed as depressions extending from the end surface 5c into the interior of the disc-shaped portion 5a. The surfaces bounding these depressions may have a matte finish which will give these surfaces the desired light-reflecting or light-scattering properties. However, an even better effect is obtained when at least a layer of light-reflective, such as white, paint is provided on the surfaces bounding the depressions.

As also seen in FIG. 4, the examining element 5 may be provided with a collecting or magnifying lens portion 12 which is advantageously pivotally mounted at the periphery of the disc-shaped portion 5a by a pivot 13, such as a screw or the like. Advantageously, the lens portion or member 12 has a lenticular region 12a and an annular cylindrical rim 12b contiguous therewith and surrounding the same. Advantageously, the focal distance of the lenticular zone 12a is about 2.5 cm.

FIGS. 5 and 7 show a modified embodiment of the examining element, here designated by the reference numeral 5". As may be seen, the examining element 5" has a plate-shaped portion 5a" which, as illustrated, is generally square-shaped with rounded-off corners, but could also be rectangular, otherwise polygonal in cross-section, or the like. Thus, the exact shape of the portion 5a", or, for that matter, of the corresponding portion 5a, is not critical, but the portion 5a" is advantageously plate-shaped. Here again, the plate-shaped portion 5a" is integral with an extension 5b" which has the above-discussed hole 6 provided therein, and an end face 5c" which is provided with a single annular formation or groove 8". It has been established that the presence of a single groove or formation 8" is sufficient for the ophthalmologist to be able to quickly estimate the symmetry or assymmetry of the cornea being examined.

Another possible modification is revealed in FIGS. 6 and 8 where it may be seen that, instead of a single groove 8", or of a plurality of concentric formations 8 or 8', a pair of parallel grooves 8a''' and 8b''' may be provided at the end face 5c''' of the element 5'''. Even this modification of the basic concept of the present invention renders it possible to easily and accurately estimate the degree of irregularity, if any, of the cornea being examined.

It may be seen that the central bore 7 is omitted in the modified examining elements 5" and 5''' shown in FIGS. 5 to 8. This is rendered possible due to the fact that the entire element 5' or 5''' is made of transparent Lucite which lets the examining physician observe the cornea therethrough with a minimum amount of distortion, even in the absence of the central hole 7.

It should be understood that formations 8", 8a''' and 8b''' could also be constituted by a series of depressions resembling those illustrated in FIG. 3, rather than by continuous grooves.

It may be seen from the above discussion that the examining element 5, which may also be referred to as a keratoscope, and the examining element 5', which may also be referred to as a corneal astigmatism indicator, as well as the examining elements 5" and 5''', are well suited for the above-discussed purposes and particularly enable the examining physician to quickly and nevertheless reliably make a diagnosis of the respective cornea. Especially, it is possible, by using the examining element 5', to obtain a qualitative indication of a corneal astigmatism and of the meridians involved.

It will be understood that, as various possible embodiments may be made of the above invention, and many changes may be made in the embodiments set forth above, all matter herein described or shown in the accompanying drawings is to be interpreted as illustrative only and not in a limiting sense. Thus, it will be appreciated by those skilled in the art that, although preferred embodiments have been shown and described, the invention is not limited thereto or thereby. Rather, the scope of protection afforded will be determined exclusively with reference to the following claims.

I claim:

1. A pocket-type instrument for determining the shape of a cornea of an eye, comprising an examining element of a transparent material having at least one light-reflective formation thereon which is centered on an axis wherein said examining element has a periphery extending parallel to the axis, the periphery having an inwardly facing light-reflective layer to reflect light rays reaching the periphery back into the examining element; and a portable source of light so positioned relative to said examining element that a light beam emitted thereby is directed transversely of said axis to illuminate said formation and to be reflected thereby onto the cornea being examined when said axis intersects the same, forming an image of the formation on the cornea, the shape of such image being indicative of the shape of the cornea.

2. An instrument as defined in claim 1, wherein said formation has an annular configuration.

3. An instrument as defined in claim 1, wherein said formation includes two separate straight-lined parallel sections.

4. An instrument as defined in claim 1, wherein said examining element is substantially plate-shaped and has two axial end surfaces; and wherein said formation is situated at one of said end surfaces.

5. The instrument as defined in claim 4, wherein said formation includes at least one depression extending from said one end surface into said examining element.

6. An instrument as defined in claim 5, wherein said formation further includes a layer of light-reflective paint in the depression.

7. An instrument as defined in claim 5, wherein said depression is a continuous circular groove.

8. An instrument as defined in claim 7; and wherein said examining element further has at least one additional continuous circular groove centered on said axis.

9. An instrument as defined in claim 5, wherein said formation includes a plurality of said depresssions spaced from one another along said formation.

10. An instrument as defined in claim 9, wherein said formation is annular; and further comprising at least one additional formation similar to said formation and radially spaced therefrom.

11. An instrument as defined in claim 9, wherein associated ones of said spaced depressions of said formations are aligned with one another radially of said axis for determining the axis of asphericity of the cornea being examined.

12. An instrument as defined in claim 1, wherein said periphery is substantially cylindrical and is centered on said axis.

13. An instrument as defined in claim 1, wherein said periphery is polyhedral.

14. An instrument as defined in claim 4, wherein said examining element has an extension projecting substantially radially from the periphery of said examining element and having a radial bore therein; and wherein said light source has a mounting portion coaxial with the beam of light emitted thereby and removably accommodated in said bore when assembled with said examining element.

15. An instrument as defined in claim 14, wherein said extension has an internal surface bounding said bore, and an external surface spacedly surrounding said internal surface; and further comprising an inwardly facing light-reflecting layer on one of said surfaces.

16. An instrument as defined in claim 1, wherein said examining element includes a substantially plate-shaped portion having said formations, and a lens portion coaxially juxtaposed with at least a region of said plate-shaped portion.

17. An instrument as defined in claim 16, wherein said portions of said examining element are discrete members; and further comprising means for displaceably mounting said discrete members on one another.

18. An instrument as defined in claim 11, wherein said mounting means includes a pivot mounting said lens member at the periphery of said plate-shaped member for pivoting relative thereto.

19. An instrument as defined in claim 1, wherein said examining element has a hole therein surrounding said axis for observation of the cornea therethrough.

* * * * *